United States Patent [19]
West

[11] Patent Number: 5,530,966
[45] Date of Patent: Jul. 2, 1996

[54] PROTECTIVE GARMENT FOR BASEBALL UMPIRES HAVING AN INNER CUSHIONED LAYER AND AN OUTER LAYER OF INTERCONNECTED PLATES

[76] Inventor: Joseph H. West, 437 Lakeview Dr., Fort Lauderdale, Fla. 33326

[21] Appl. No.: 416,688

[22] Filed: Apr. 10, 1995

Related U.S. Application Data

[63] Continuation of Ser. No. 994,497, Dec. 21, 1992, abandoned.

[51] Int. Cl.$^6$ ............................................. A41D 13/00
[52] U.S. Cl. .............................................. 2/2; 2/25
[58] Field of Search ..................... 2/2, 2.5, 44, 45, 2/268, 267

[56] References Cited

U.S. PATENT DOCUMENTS

| | | |
|---|---|---|
| 3,452,362 | 7/1969 | Korolick et al. . |
| 4,453,271 | 6/1984 | Donzis . |
| 4,486,901 | 12/1984 | Donzis . |
| 4,513,451 | 4/1985 | Brown . |
| 4,554,681 | 11/1985 | Kirkland . |
| 4,590,622 | 5/1986 | Wolfe et al. . |
| 4,602,385 | 7/1986 | Warren . |
| 4,698,846 | 10/1987 | Wang . |
| 4,847,913 | 7/1989 | Chen . |
| 4,872,215 | 10/1989 | Sliger . |
| 4,872,216 | 10/1989 | Wingo, Jr. . |
| 4,996,720 | 3/1991 | Fair . |
| 5,020,156 | 6/1991 | Neuhalfen . |
| 5,029,341 | 7/1991 | Wingo, Jr. . |
| 5,054,121 | 10/1991 | Mitchell . |
| 5,060,313 | 10/1991 | Neuhalfen . |
| 5,107,542 | 4/1992 | Zide et al. . |
| 5,187,812 | 2/1993 | Neuhalfen . |

OTHER PUBLICATIONS

Letter dated Apr. 13, 1993 from Ben D. Tobor, Esq. of McGlinchey Stafford Lang to John S. Child, Jr., Esq.
Affidavit of Mr. Roger Douglas.
Affidavit of Mr. Brian Donzis.

*Primary Examiner*—John J. Calvert
*Assistant Examiner*—Gloria Hale
*Attorney, Agent, or Firm*—Dann, Dorfman, Herrell and Skillman

[57] ABSTRACT

A protective garment for the torso of a body and in particular a chest protector for baseball umpires which has an inner flexible layer and outer shell layer. The inner layer is in the form of a flexible pad adapted to conform to the contour of the torso. The inner layer has an inner and outer surface and an intermediate thickness of cushioning material adapted to distribute impacts against a given area of the outer layer over an area of the inner layer which is at least as great, as said given area. The outer shell layer is adapted to overlie said inner layer and comprises a plurality of interconnected plate elements. Each plate element is positioned and arranged to overlie a selected area of the torso. The garment also has both flexible straps and a cover element for interconnecting the plate elements to form a torso-fitting outer shell and releasable fasteners to interconnect the inner layer and outer shell layer. The releasable fasteners include anchor straps which pass through a pair of spaced-parallel slots in the plate elements and are releasably connected together between the pair of slots.

24 Claims, 7 Drawing Sheets

PROTECTIVE GARMENT FOR BASEBALL UMPIRES HAVING AN INNER CUSHIONED LAYER AND AN OUTER LAYER OF INTERCONNECTED PLATES

RELATED APPLICATION

This application is a continuation of U.S. application No. 07/994,497, filed Dec. 21, 1992, abandoned.

FIELD OF THE INVENTION

The field of the invention is directed to a protective garment for the torso of the body for use in athletic activities. The protective garment is particularly designed for use as a chest protector for baseball umpires.

BACKGROUND OF THE INVENTION

Protective garments for athletes are specifically designed to accommodate the hazards of a particular sport or activity. For example, football pads are designed to protect against body impacts while permitting the player to perform the maneuvers required on the football field. Lacrosse pads are designed to protect against limited body impact but also against impact from lacrosse sticks and balls, while allowing the athlete to perform the maneuvers required by the game. In many cases, the padding may be specifically designed for a particular playing position. For example, the pads for goaltenders are normally quite different than those for the players at offensive and defensive positions. In baseball, the catcher has a chest protector and shin pads.

The invention is directed to a protective garment for use in athletic activities and particularly to a chest protector of the type used by umpires in baseball games. For umpires, the invention is designed to protect the wearer from being injured by the force impact from a baseball as might normally occur when the baseball is "foul-tipped" by a batter. Such "foul-tips" often strike an umpire and conventional chest protectors have been used in the past to reduce such injury.

Conventional baseball catchers' chest protectors are frequently manufactured by placing small pieces of foam between front and back pieces of fabric, sometimes gluing the foam in place. The pieces of fabric are generally stitched to each other along the peripheral border, in voids between the pieces of foam, and sometimes through the foam. Some chest protectors utilize cotton which is simply pushed into hollow ribs or chambers of fabric and appropriately stitched. The process of manufacturing such conventional chest protectors is labor intensive and time consuming and the protection offered is minimal at best.

Such traditional or conventional chest protectors are designed to absorb the force of impact so as to allow the ball to drop to the ground and to prevent the ball from ricochetting, and are not designed to diffuse the force of impact created by the forceful contact of a high-speed baseball. This deficiency is apparent particularly with respect to the conventional chest protectors referred to above which include a plurality of spaced or separated hollow ribs. The spacing between the ribs offers no protection to the wearer of such conventional chest protectors.

Another common form of chest protector used by umpires is of an inflatable type in which pressurized air is used to inflate a protective jacket. Use of pressurized gas requires the use of a compressor or mechanical pump to properly inflate the jacket. This additional equipment adds significantly to the cost and inconvenience of using such a jacket. Furthermore, because a significant quantity of pressurized air is needed to inflate the protective jacket to a pressure which provides the desired protection against impact, the jacket tends to be extremely bulky.

Conventional chest protectors also tend to be formed as a single unit, though made of a plurality of pieces, and are difficult and inconvenient to transport, pack and wear.

Protective garments have also been developed for non-athletic activities to protect the wearer from various injurious and even life-threatening hazards. For example, U.S. Pat. No. 3,452,362 to Korolick et al. relates to a flexible body garment consisting of front and back portions each of which contains a pocket to receive an armor plate. Similarly, U.S. Pat. No. 4,602,385 to Warren relates to a vest or garment constructed of a laminated material which has thermal protective, shock absorptive and puncture resistant properties. The patented garment includes a body portion that is quickly connectable about the torso of the user with front and back panels that are hingedly connected together. The garment also includes a hood or head portion that is hingedly connected to the back panel of the body portion.

Protective garments for athletic activities have also been described in the literature. For example, U.S. Pat. No. 4,872,115 to Sliger relates to a chest protector for use in sporting events such as karate or other martial arts in which maneuverability is required. The Sliger protector is sized to cover the chest and abdomen of its wearer. The protector has an outer layer formed of a light-weight leather or leather-like material, an inner layer formed of batting, and closed-cell foam pads provided intermediate the inner and outer layers.

Protective garments for contact sports such as football are referenced in U.S. Pat. No. 4,486,901 to Donzis, U.S. Pat. No. 4,872,216 to Wingo, Jr., U.S. Pat. No. 4,996,720 to Fair and U.S. Pat. No. 5,107,542 to Zide et al. The Donzis patent relates to pads which cushion the impact by regulating the escape of air from the foam layer of the shielded shock-absorbing structure. The shield is a single plate removably mounted on the fabric-covered foam layer of the structure. The Wingo patent relates to a cantilever strap for a shoulder pad for a football player. In the Wingo patent, the central portion of each cantilever strap which overlies the acromio-clavicular area of the football player's shoulder is substantially greater than two inches in width to disperse force from an impact on that area. The Fair patent relates to a protective vest having an upstanding collar or neck guard intended for contacting the bottom edge of a player's helmet. The vest has a flexible body with shoulder portions between chest and back panels. The vest may consist of a one-piece foam material or the foam material coated with a moisture barrier. The Zide patent relates to a front-lock stabilizer for protective shoulder pads for football. The pads comprise breastplates and backplates. The breastplates are closed by laced interdigitated plates fixedly secured to the vertical edges of the breastplates. The backplates are closed by a plurality of rigid plates extending between the backplates and fixedly secured thereto.

Protective garments for use in baseball are referred to in U.S. Pat. No. 4,847,913 to Chen and U.S. Pat. No. 5,020,156 to Neuhalfen. The Chen patent relates to a chest protector formed by a pair of chest protector bodies, each of which is formed to include a one-piece, homogeneous, in situ molded foamed polymeric/copolymeric material. A zipper is disposed along a vertical line of the protector for securing the protector bodies to each other. Straps are also provided for securing the chest protector bodies to each other along the back of a user. The Neuhalfen patent relates to a chest protector for a baseball catcher. The protector has a hinged shoulder pad covering one shoulder and the upper portion of one arm of the catcher. This protector is designed in part to protect the shoulder and upper part of the throwing arm of the catcher without interfering with the catcher's throwing motion. The Neuhalfen protector also comprises a one-piece substantially flat pad formed by an outer casing and a shock-absorbent cushion. This pad is adapted to cover the chest, stomach and shoulders of the catcher.

SUMMARY OF THE INVENTION

It is an object of the invention to provide a protective garment that is not bulky and maintains the maneuverability of the wearer.

It is another object of the invention to provide an improved protective garment that diffuses the force of impact on the wearer created by the forceful contact of a high-speed baseball.

It is another object of the invention to provide a protective garment that is separable into two or more parts that are more convenient to transport and pack. The inner part or component may be replaced with a fresh component if it becomes damaged or soiled in use, or if its protection characteristics deteriorate from age or exposure to severe ambient conditions.

Preferably, the invention provides a protective garment that does not have to be inflated and does not require the use of pressurized gas.

The protective garment of the invention has two layers which comprise a flexible inner layer and a hard outer layer which is adapted to be removed from the inner layer to facilitate replacement or repair of either or both layers.

Preferably, the inner layer is in the form of a flexible pad adapted to conform to the contour of the torso. The inner layer has an inner surface adapted to confront the torso and an outer layer facing outwardly from the torso. The inner layer includes an intermediate thickness of a cushioning material adapted to distribute impacts against a given area of the outer layer over an area of the inner layer which is at least as great as said given area. Preferably, the hard outer layer is in the form of a shell adapted to overlie said inner layer and comprises a plurality of interconnected plate elements. Each of these plate elements is preferably positioned and arranged to overlie a selected area of the torso and includes means for interconnecting said plate elements to form a torso-fitting shell overlying said inner layer.

Preferably, the means for interconnecting the plate elements comprise at least one flexible strap spanning between adjacent plate elements. This flexible strap may have one end connected to one plate element and the other end connected to an adjacent element. The strap is preferably of a length to provide a clearance space between the adjacent elements to afford hinge-like displacement of said adjacent plate elements.

In one of the preferred embodiments of the invention, the interconnecting means also includes a second plate connector overlying other plate elements positioned in edge-confronting adjacent relation. This second plate connector comprises a cover element overlying the confronting marginal edges of said two other plate elements. Preferably, this cover element is interconnected with each of said two other plate elements along said confronting marginal edges of said two other plate elements. It is desirable that the cover element is made of a stiff shock-resistant lightweight material. In addition, in the area of this cover element, the shell provides a substantially rigid interconnection between said two other plate elements with an area of multiple thicknesses along each of the confronting marginal edges of said two other elements.

In each of the preferred forms, at least two of said plate elements include at least one pair of eyelets comprising spaced-parallel slots penetrating through said associated plate. The outer layer or shell is thereby connected to said inner layer by anchor straps. The straps may be mounted on the inner layer and extend through said spaced-parallel slots. Preferably, the straps have releasable means to releasably mount said shell on said inner layer.

These and other objects of the invention will be set forth in more detail in the following description when read in conjunction with the drawings, in which:

DESCRIPTION OF THE PREFERRED EMBODIMENTS

FIGS. 1–8 illustrate a first embodiment of the invention which is particularly suited for use by baseball umpires. The protective garment of FIGS. 1–8 covers the entire frontal area of the upper torso to provide protection against impacts from baseballs which may be "foul tipped" by the batter.

Figure 3:
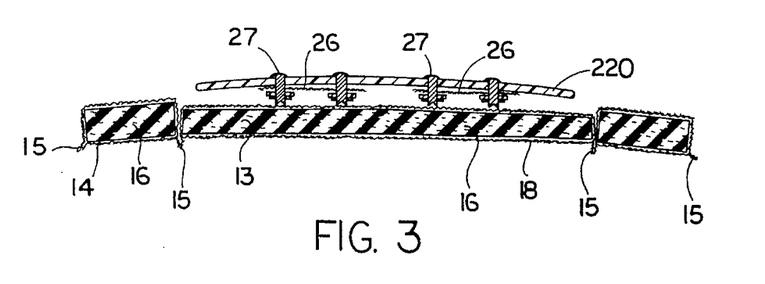
FIG. 3 is a sectional view taken on the line 3—3 of FIG. 1.
Figure 4:
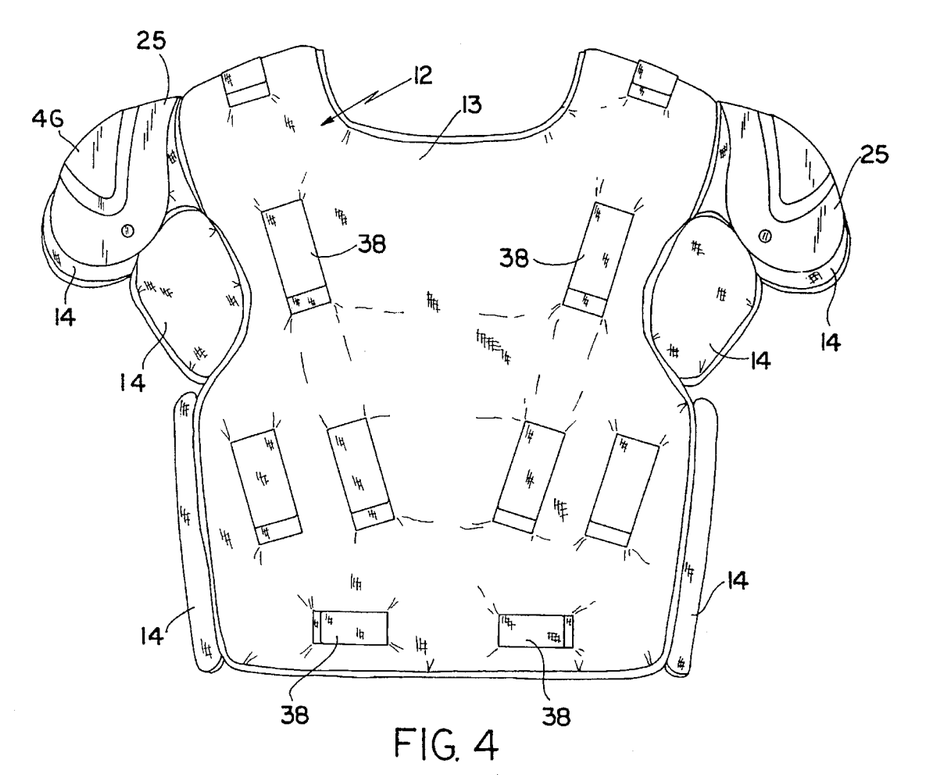
FIG. 4 is a front elevation of the first protective garment with the outer layer removed.
Figure 5:
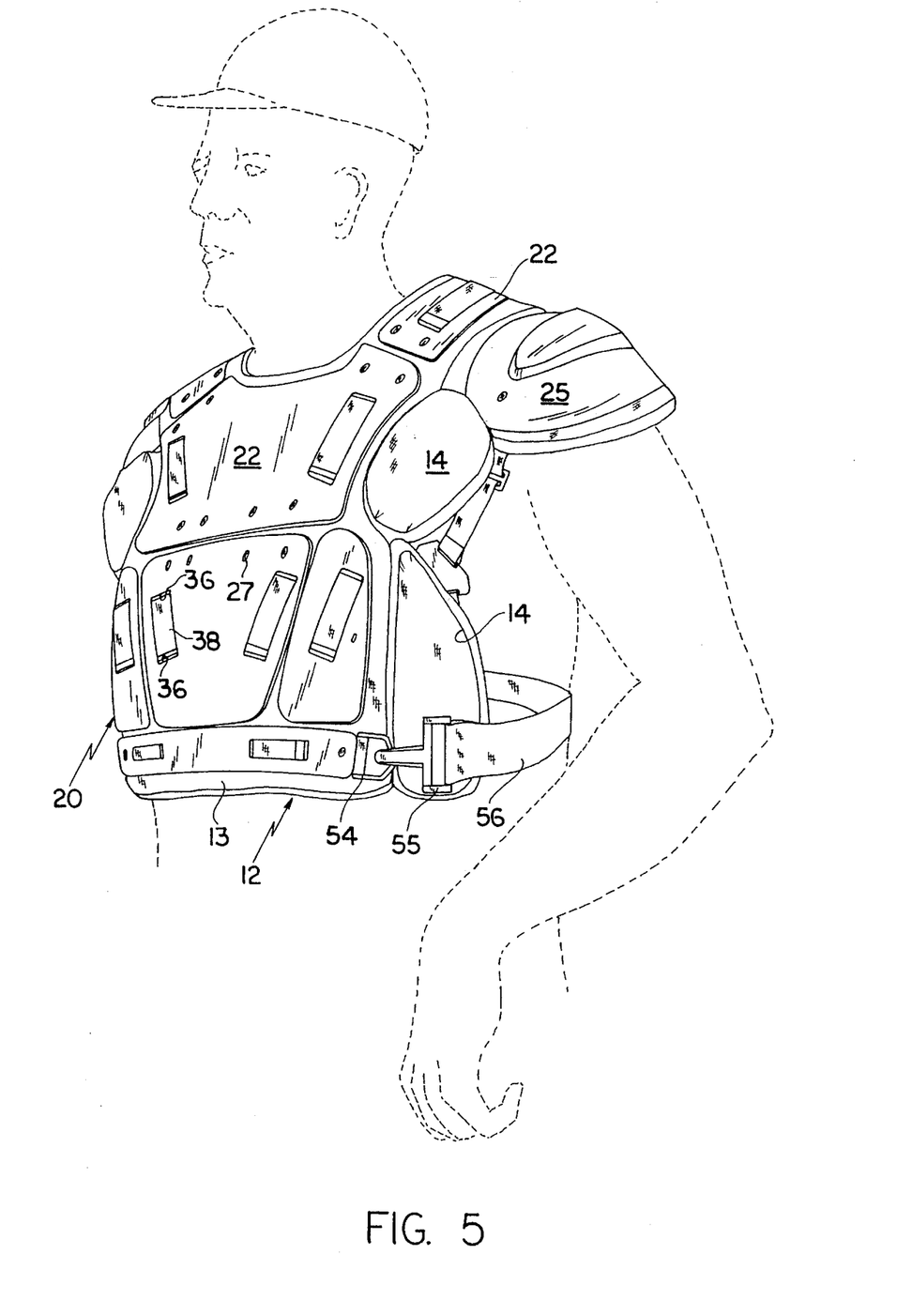
FIG. 5 is a perspective view of the garment illustrated in FIG. 1, as worn by an umpire.

The protective garment has an inner layer 12 comprising a frontal pad 13 extending from the shoulder to below the waist and supplemental wing pads 14 adapted to overlie the shoulders, the armpits, and the sides of the torso, respectively. Each of the pads 13 and 14 comprises a thickness of flexible cushioning material 16 enclosed in a fabric sheath 18. In the present instance, the sheath 18 encloses the cushioning material 16 and is provided with a seam around its entire perimeter forming a peripheral flange 15. In the present instance, the wing pads 14 are connected to the frontal pad 13 by interconnecting the respective flanges of the frontal pad and the wing pads along the line where they are interconnected so as to provide an articulated cover which may be folded generally along the seam lines between the respective pad elements of the inner layer 12. As shown in FIG. 3, the cushioning material 16 in the frontal pad 13 is of a different character than the cushioning material 16 in the wing pads 14, as will be described more fully hereinafter. In the present instance, the seams 15 are positioned along the inner surface of the respective pads so that the wing pads may be readily folded inwardly and will naturally follow the contour of the upper torso of the user.

Overlying the inner layer 12, an outer shell 20 is releasably secured to the inner layer 12 to afford a distribution of the forces of impact over a wide area of the inner layer. The outer shell 20 comprises a plurality of interconnected plate elements 22 and supplemental plate elements 23, 24 and 25. The plate element is identified by the generalized character 22 and comprises an intermediate breastplate element 220, a solar element 221 and shoulder elements 222. The supplemental plate elements 23 are releasably secured to the frontal pad 13 in the side area. The supplemental plate element 24 is connected to the frontal pad 13 along the lower edge thereof and the supplemental plates 25 are mounted on the wing pads 14 which overlie the shoulder area. In the present instance, the plates 23 and 24 are releasably mounted on the frontal pad 13 and the supplemental plate 25 is permanently mounted on the shoulder wing pad 14.

The interconnected plates 22 are hingedly connected by flexible straps 26 which are riveted to the plates 220, 221 and 222 as indicated at 27, so as to position the adjoining plates close to each other but with a clearance space therebetween. As shown, the clearance space is less than the diameter of a baseball. The flexible straps 26 are of a fabric construction which affords a freedom for hinged movement of the plates about a hinge axis extending within the clearance space generally parallel to the confronting edges of the adjoining plates. The hinged movement of the plates relative to one another is limited when the plates are secured to the underlayer 12, but the plates are free for hinged movement when released from the underlayer 12. The fabric construction of the straps 26 resists twisting movement.

The shell layer 20 is adapted to be releasably mounted on the underlayer 12 so that the layers may be disassembled for packing and storing or for cleaning or repair. When disassembled, the inner layer may be cleaned or, if necessary, dried out, for example when the layer has become wet from perspiration or from adverse weather conditions. To provide the desirable releasable interconnection, anchor straps 38 are secured to the inner layer 12 and project outwardly through a pair of eyelets in the form of spaced parallel slots 36 within the plates 22, 23 and 24. The anchor straps 38 are connected to the frontal pad 13 of the inner layer 12 by stitching 37 which passes through the inner pad including both the sheath 18 and the padding 16. The stitching 37 not only secures the anchor strap 38 in place on the pad 13, but also serves to tack the padding 16 in place within the sheath 18. The straps 38 are thereby anchored to the pad 13 at one end and extend through the spaced parallel slots 36 and may be overlapped at their other end and interconnected by suitable fastening means 42. In the present instance, the fastening means 42 comprises complementary hook and loop strips of the "VELCRO" type which provide a secure interconnection between the free ends of the anchor straps 38 and yet are readily releasable to free to outer shell 20 for removal from the inner layer 12. For ease of manufacture, the anchor straps may be formed in pairs, one element of the pair being provided with flexible hooks and the other element of the pair being provided with loops. Alternate fastening means may be employed such as pressure-sensitive adhesive, hooks and eyes, snaps, etc. However, anchor strips of complementary hook and loop fabrics are used in the preferred embodiments of the invention.

Figure 1:
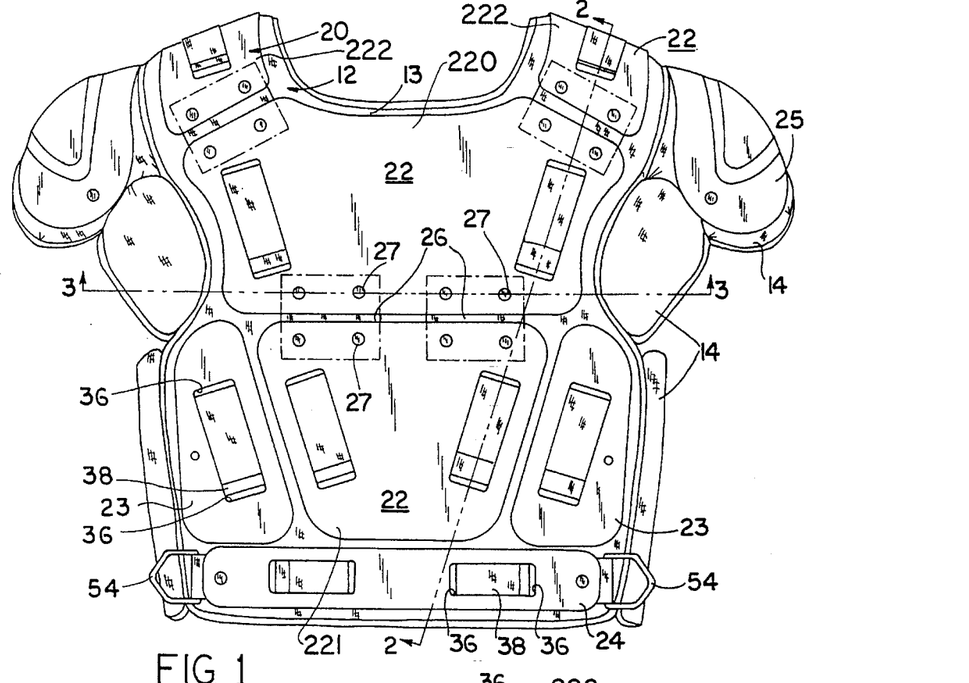
FIG. 1 is a front elevation of a first protective garment embodying the invention.

As shown in FIGS. 1 and 3, the interconnected plates comprise an intermediate breastplate 220 with shoulder plates 222 hinged on opposite sides of the upper portion thereof and a solar plate 221 hinged along the bottom edge thereof. The intermediate breastplate 220 extends across the full width of the underlayer 12 in the area between the armpits. As noted above, wing pads 14 are connected to the frontal pad 13 and extend beyond the sides of the intermediate breastplate 220.

Each of the plates 22 comprises a sheet of stiff, shock-resistant, lightweight material which may be a synthetic plastic or other suitable material. The intermediate plate 220 is designed to accept the impact of foul tips and to diffuse the force of the impact over the wide area of the plate 22. This diffuse force is cushioned by the entire underlying area of the frontal pad 13. As shown in FIG. 3, the cushioning material 16 in the frontal pad 13 underlying the plate 22 is a high density foam material which is designed to provide substantial protection against impact and to absorb the force which has been diffused by the plate. The wing pads, on the other hand, are of thicker material which is less dense and provides a greater cushioning affect by reason of the fact that the area protected by the wing pads is not as susceptible to direct impact from foul tips, allowing the less dense foam material 16 in the wing pads to protect the armpit area of the user.

Figure 6:
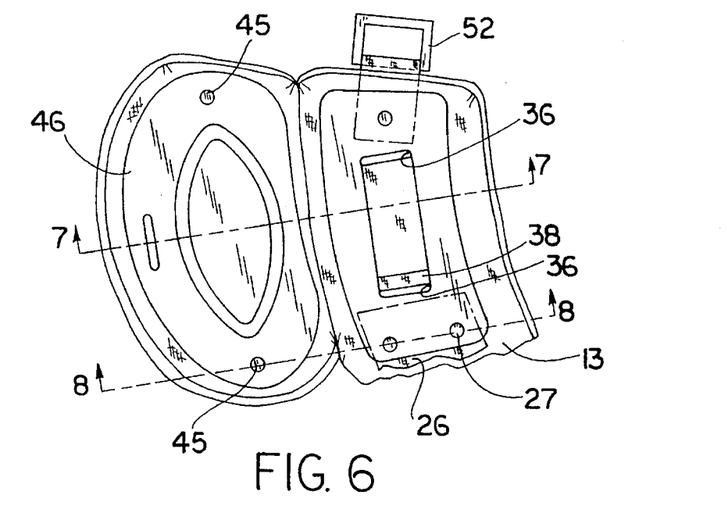
FIG. 6 is a fragmentary top view of the protective garment of FIG. 1, illustrating its shoulder protection.
Figure 7:
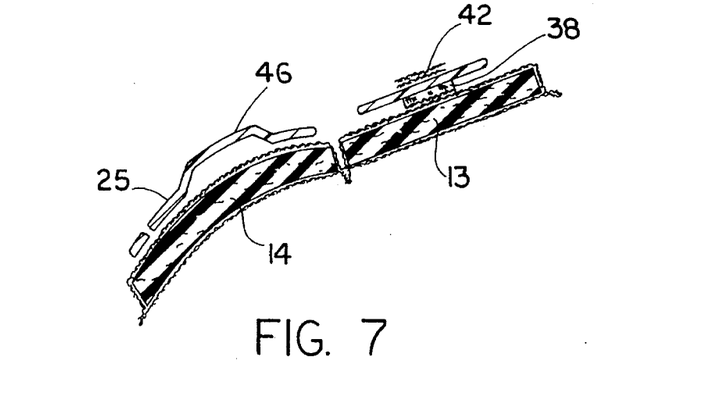
FIGS. 7 and 8 are sectional views taken on the lines 7—7 and 8—8 of FIG. 6.
Figure 8:
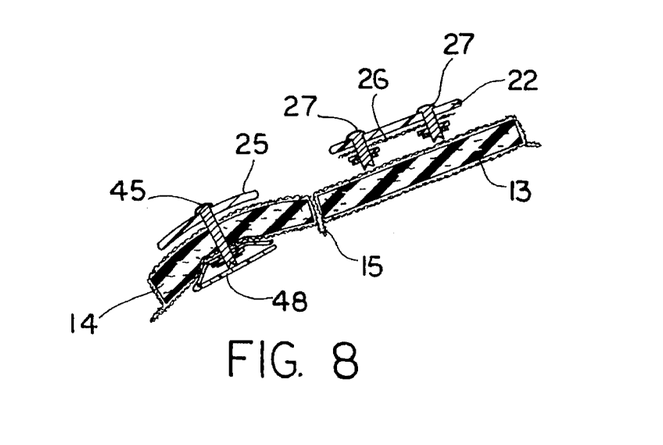

As shown in FIGS. 6–8, the wing pad for the shoulders is of the same material as the frontal pad 13 because of the presence of the shoulder plate 25 which functions to diffuse the impact of foul tips over the wide area of the high-density cushioning material 16 in the shoulder wing pad 14.

The shoulder plate 25 differs from the other plates 22, 23 and 24 not only by reason of the fact that the plate is permanently secured to the shoulder wing pad 14 by rivets 45 (see FIGS. 6 and 8) but also in that the plate is reinforced centrally by an upstanding central portion 46 which serves to reinforce the plate against deflection, i.e. denting or bending. Since the rivets 45 penetrate the wing pad 14, as shown in FIG. 8, the underside of the rivet is protected by a suitable shielding cover 48 and the cushioning material within the wing pad 14 is compressed in the area of the rivet so that any impact against the plate 25 is borne by the cushioning material surrounding the rivet rather than by the rivet itself.

The protective garment is designed to be retained on the torso by straps connected to the shell 20. To this end, the shoulder plates 22 have eyelets 52 at the back thereof to receive shoulder straps of the harness and the lower supplemental plate 24 is likewise provided with strap loops 54 to accommodate belt hooks 55 of the supporting harness 56 shown in FIG. 5. Thus, the protective garment shown in FIGS. 1–8 inclusive may be readily donned and doffed by unhooking the harness 56 from the outer shell 20 and then removing the assembled shell and inner layer from the torso. With the assembly removed, the shell 20, including the supplemental plates 23 and 24, may be removed from the inner layer 12. The connections provided by the anchor straps 26 enables the removed shell to be folded up for storage or shipment, and the inner layer 12 may also be folded for shipping or storage or may be cleansed, dried out, or otherwise treated. The present invention permits the user of the garment to substitute fresh padding when the original padding deteriorates, either through use or age. Furthermore, the invention permits the inner layer 12 to be custom-designed for the individual users, while permitting the fabrication and use of a standardized outer shell for purposes of economy.

The invention is not limited to the particular configuration shown in FIGS. 1–8, but the invention may be used in other configurations. For example, a second protective garment constructed in accordance with this invention is generally designated by the reference number 110 in FIGS. 9–15.

As shown in FIGS. 9 through 15, the protective garment is designed to be worn over the torso of a user. The protective garment has an inner layer 112. The inner layer is in the form of an unitary, flexible pad covering the entire upper frontal area of the user and adapted to conform to the contour of the torso. The inner layer comprises an inner surface 114 adapted to confront the torso, an intermediate cushioning material 116 and an outer surface 118 facing outwardly from the torso. The inner and outer surfaces 114 and 116 comprise a sheath made of fabric and generally of the same fabric. A clothing fabric that is water-resistant such as rip-stop nylon is preferred. The cushioning material 116 is made of a relatively soft flexible material and has a thickness and resilience adapted to distribute impacts against the outer surface 118 over a larger area of the inner surface 114. The sponge-like cushioning material 116 is preferably foam rubber, convoluted foam, or a compressible closed-cell foam material which does not age harden when exposed to the moist heat generated by the body or the heat which is normally present in sports stadiums where the protective garment is likely to be worn. It should be understood that the selection of a cushioning material may be modified according to the ultimate end use for which the garment is designed. In the present instance, the foam rubber cushioning material has a thickness on the order of ⅝". In the present instance, the cushioning layer 116 is enclosed in a fabric sheath formed of rip stop nylon fabric or the like which is resistant to tearing or damage. Preferably, the fabric forming the inner surface 114 of the layer 112 extends beyond the perimeter of the cushioning material 116 to provide a peripheral flange 115 extending about the entire perimeter of the layer 112.

Figure 12:
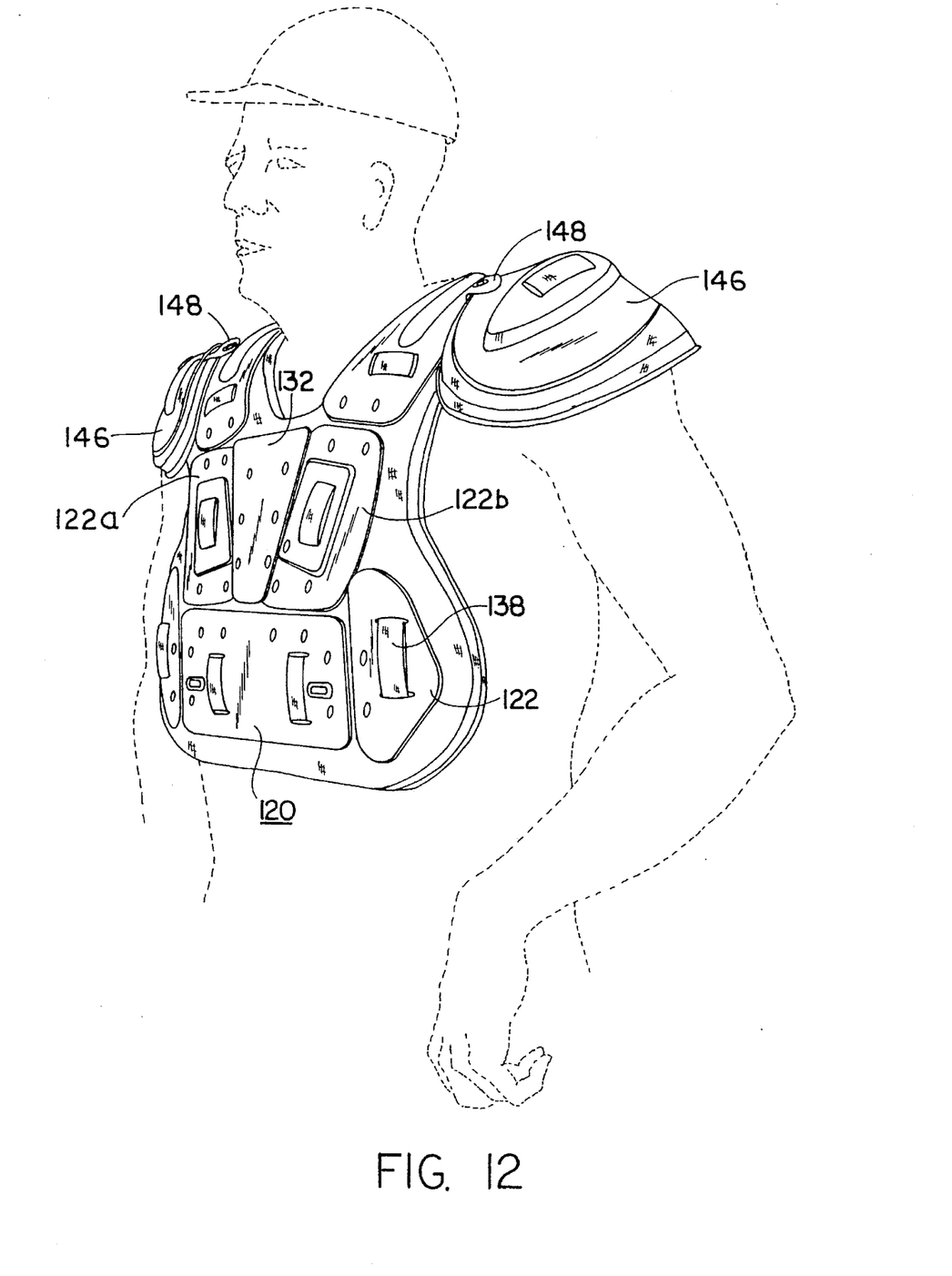
FIG. 12 is a perspective view of a protective garment of FIG. 9, as worn by an umpire.

An outer shell layer 120 is mounted over the outer surface 118 of the inner layer 112. The outer shell layer includes a number of interconnected plate elements 122. Each of the plate elements overlies a selected portion of the torso. In the present instance, selected plates are adapted to overlie the rib cage, the sternum, the clavicle, the scapula, and the shoulder joint. The plate elements are also adapted to fit smoothly over substantially the entire upper frontal area of the torso as shown in FIG. 12.

Figure 9:
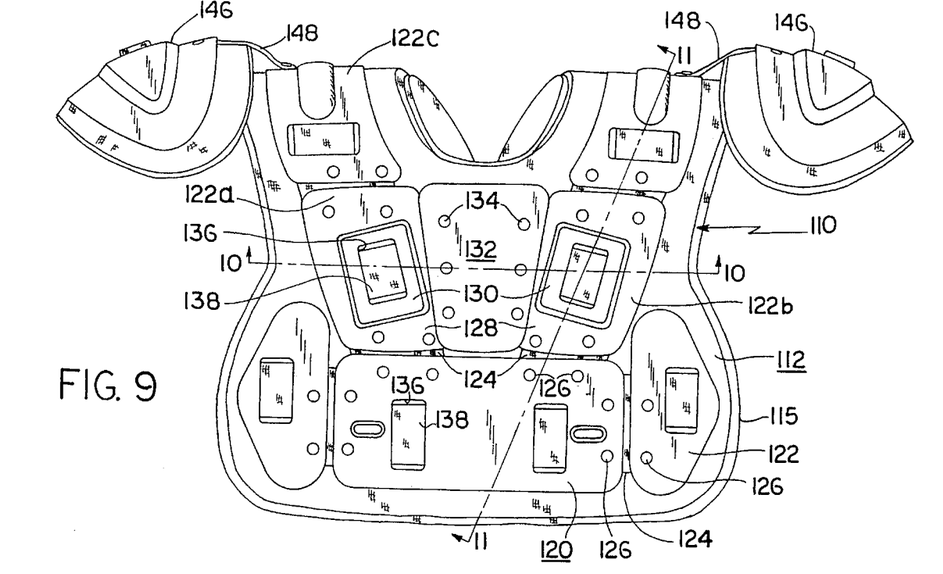
FIG. 9 is a front elevation of a second embodiment of a protective garment embodying the invention.

As shown in FIG. 9, each plate element is interconnected to an adjacent plate element by a flexible strap 124. This interconnection is carried out by means of rivets 126 which extend through the plate element and strap. The strap provides a clearance space between the adjacent plate elements to afford hinge-like displacement of the associated plate elements 122 about a hinge axis which extends generally parallel to the confronting edges of the two adjacent plates within the clearance space. As in the first embodiment, the clearance space is less than the diameter of a baseball and the straps 124 are of a width and stiffness so as to resist flexing of the straps except along the hinge axis.

Figure 2:
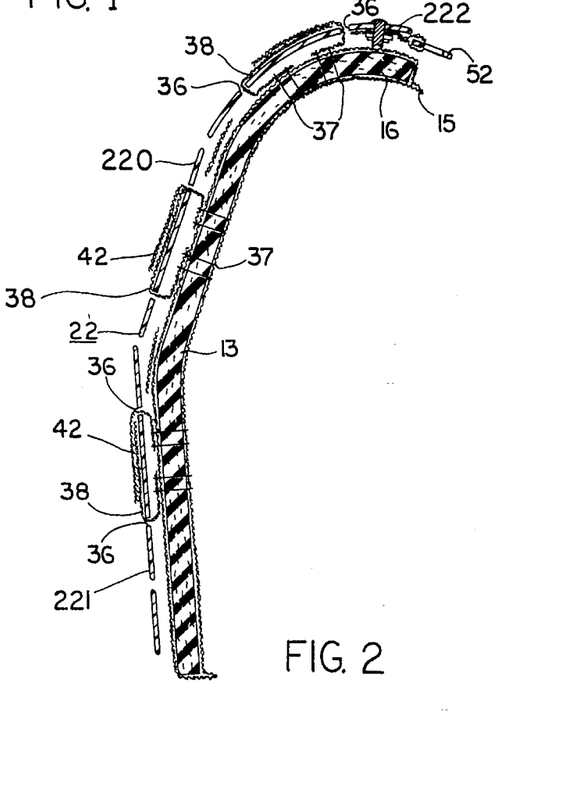
FIG. 2 is a sectional view taken on the line 2—2 of FIG. 1.

The outer shell layer of this second embodiment also includes an intermediate component having a second plate connector positioned between two plate elements which overlie the sternum and which are designated 122a and 122b in FIGS. 1 and 2. The intermediate plate connector comprises a cover element 132 which overlies the confronting marginal edges of the intermediate plate elements 122a and 122b. The cover element is interconnected with each of the elements 122a and 122b by rivets 134 positioned along such confronting marginal edges.

Figure 10:
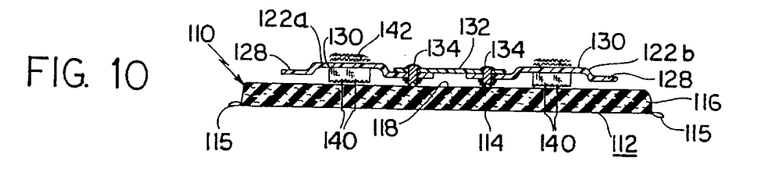
FIG. 10 is a sectional view taken on the line 10—10 of FIG. 1.

Both the cover element 132 and intermediate plate elements 122a and 122b comprise a sheet of a stiff shock-resistant lightweight material which may be a synthetic plastic or other suitable material. In the area of the cover element 132, the shell of this embodiment of the invention provides a substantially rigid interconnection between the intermediate plate elements 122a and 122b, producing an area of multiple thickness along each of the confronting marginal edges of the plate elements. As shown in FIGS. 9 and 10, the marginal edges of the plate elements 122a and 122b are substantially flat and coplanar as shown at 128 and surround a central portion 130 which is elevated. The elevated portion has a height greater than the thickness of the cover element 132 so that, when assembled as shown, the overlapped elements do not project outwardly beyond the elevated central portions 130 of the elements 122a and 122b. The elevated central portions 130 provide additional stiffness to the plates 122a and 122b and serve to reinforce these plates against deflection.

The cover element 132 and the elements 122a and 122b are adapted to overlie the sternum or breastbone. The area of multiple thickness and elevated central portion constitute the area of the protective garment providing the greatest diffusion of the force of impact created by the forceful contact of a high speed baseball. The greater protection offered by this central portion of the protective garment of this embodiment of the invention is in recognition that the breastbone is the part of the torso most vulnerable to the force of the impact referenced above.

Figure 11:
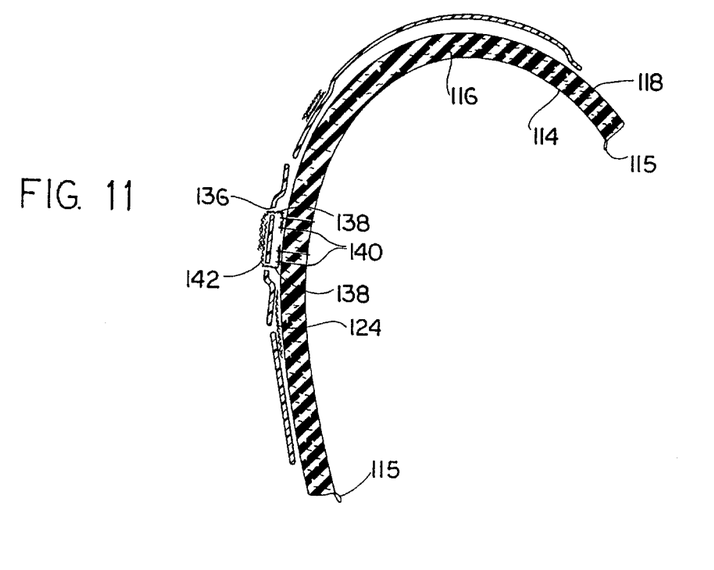
FIG. 11 is a sectional view taken on the line 11—11 of FIG. 1.
Figure 13:
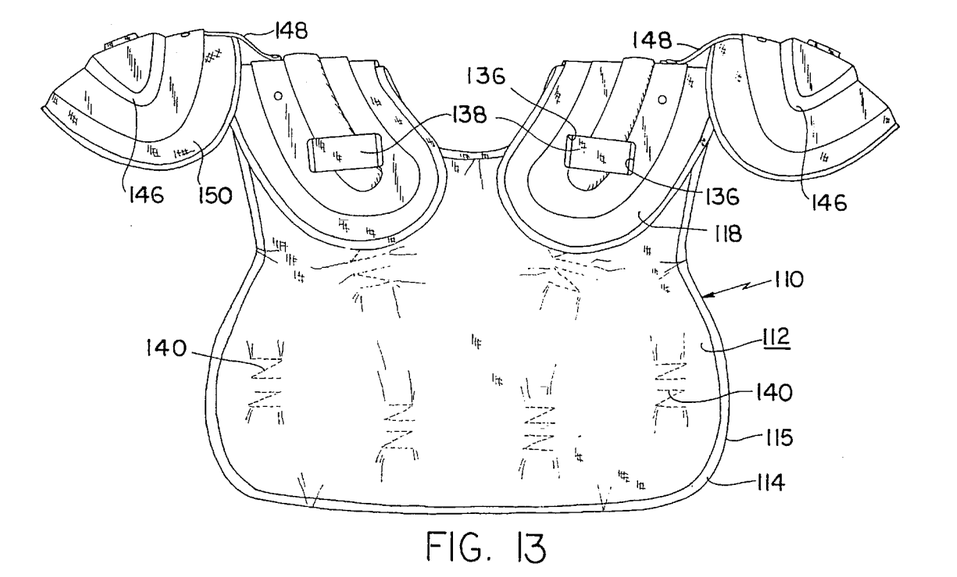
FIG. 13 is a rear elevation of a protective garment of FIG. 9.

Preferably, the shell 120 is releasably mounted on the inner layer 112, so that it may be disassembled for packing and storing, or for cleaning or repair. The hinged interconnection of the plates 122 enable the shell 120 to be folded on itself to provide a more compact package. The flexible nature of the inner layer 12 permits the layer to be folded upon itself when it is disassembled from the shell. When disassembled, the inner layer may be cleaned or, if necessary, dried out, for example when the layer has become wet from perspiration or from adverse weather conditions. To provide the desired releasable connection, anchor straps 138 are secured to the inner layer 112 and project outwardly through a pair of eyelets in the form of spaced parallel slots 136 penetrating through the associated plate 122. As shown in FIGS. 10, 11 and 13, the anchor straps 138 are mounted on the inner layer, for example by stitching at one end which penetrates through the layer as indicated diagrammatically at 140, and project through the spaced parallel slots and have releasable fastening means at 142 in FIG. 11. Preferably, the fasteners 142 comprise hook and loop fastener strips, but other devices, such as releasable adhesive surfaces may be provided on the ends of the straps 138 to releasably mount said shell on said inner layer.

When it is desired to separate the shell 120 from the layer 112, the fasteners 142 may be released and the straps 138 may be withdrawn through the slots 136. When all of the anchor straps are released, the shell 120 may be simply lifted from the underlayer 112.

Figure 14:
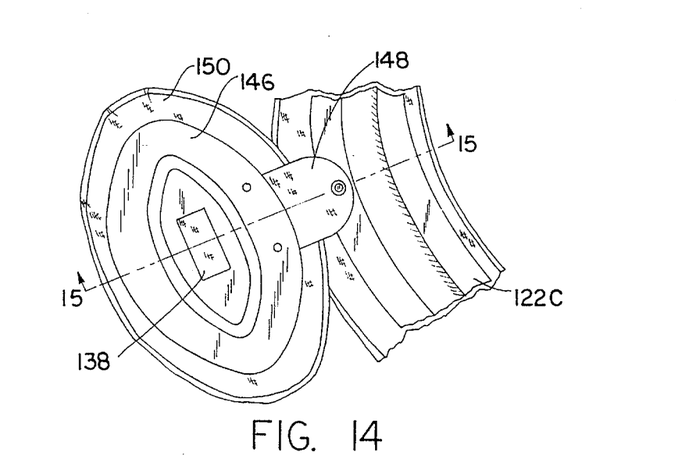
FIG. 14 is a fragmentary top view of a protective garment of FIG. 9, showing its shoulder protection.
Figure 15:
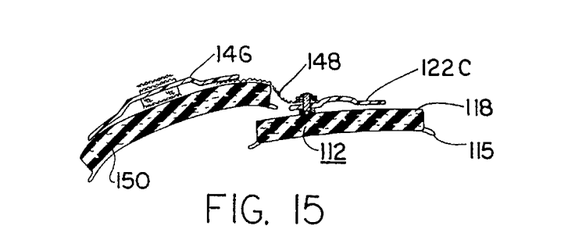
FIG. 15 is a sectional view taken on the line 15—15 of FIG. 14.

As shown in FIGS. 14 and 15, a shoulder protector 146 for each shoulder is connected to the chest portion of the outer shell by a flexible strap 148. The strap is of a length to provide clearance space between the pad and the portion of the shell to afford double-hinged movement of said additional plate element relative to said shell, i.e., about the rivet axis perpendicular to one of said plates as well as about a hinge axis which falls within the clearance space along the confronting edges of the plates 146 and 122c. Each shoulder pad comprises an inner layer and plate element similar in construction to the inner layer 112 and shell layer 120 of the chest portion. In this embodiment, the plate 146 is releasably connected to the underlying pad 150 by anchor straps 138 which pass through slots in the plate 146 and have releasable interconnecting means similar to the means described above at 142. The underlying pad 150 is separated from the inner layer 112 and remains assembled to the protective garment by reason of its releasable interconnection with the plate 146 and the double-hinged connection of the plate 146 to the plate 122c which, in turn, is releasably anchored to the underlayer 112 by the several anchor straps 138. Thus, the double-hinged connection between the plates 146 and 122c provides ample freedom for movement of the shoulder and the upper arm of the person wearing the garment.

While particular embodiments of the present invention have been herein illustrated and described, it is not intended to limit the invention to such disclosure and changes may be made thereon and thereto within the scope of the following claims.

I claim:

1. A protective garment for the torso of a body for use by baseball umpires comprising in combination an inner layer in the form of a flexible pad adapted to conform to the contour of the entire frontal area of the upper torso and having an inner surface adapted to confront the torso, an outer surface facing outwardly from the torso, and a perimeter defining the outlines of said inner and outer surfaces, said layer including an intermediate thickness of cushioning material between said inner and outer surfaces, an outer shell layer covering substantially the entire frontal area of the upper torso and adapted to overlie said inner layer within its perimeter and comprising a plurality of interconnected plate elements, each plate element being positioned and arranged to overlie a selected area of the torso, and means interconnecting said plate elements to form a torso-fitting shell overlying said inner layer, said cushioning material adapted to distribute impacts against a given area of the outer layer over an area of the inner layer which is at least as great as said given area, said interconnecting means comprising at least one flexible strap spanning between adjacent plate elements of said plurality, said strap having one end connected to one element and the other end connected to the adjacent element and being of a length to provide a clearance space between the adjacent elements to afford hinge-like displacement of said adjacent plate elements about a hinge axis within said clearance space, said clearance space being limited to less than the diameter of a baseball whereby said inner layer, in the entire frontal area of the upper torso is protected against direct impact by a baseball, each of said plate elements being a stiff, shock-resistant, lightweight material, having releasable fastening means interconnecting said shell on said inner layer.

2. A protective garment according to claim 1 wherein said releasable interconnecting fastening means comprise a pair of anchor straps passing through said shell and hook and loop fasteners on the respective anchor straps of said pair.

3. A protective garment according to claim 1, said plurality of plate elements comprising two arcuately-formed shoulder plates adapted to overlie the collarbone, at least one breastplate adapted to overlie the breastbone or sternum, and a front plate adapted to overlie the solar plexis within the rib cage and below the sternum wherein said outer shell extends continuously across the full width of the frontal area of the upper torso from the solar plexis to the collarbone.

4. A protective garment according to claim 1 wherein said cushioning material comprises a compressible closed-cell foam material contained within a fabric sheath.

5. A protective garment according to claim 4 wherein said sheath has a peripheral flange projecting beyond the perimeter of said cushioning material about its entire periphery.

6. A protective garment according to claim 5 wherein said cushioning material comprises a unitary pad underlying all of said interconnected plate elements of said shell and extending continuously from the solar plexis to the collarbone.

7. A protective garment according to claim 6 wherein said releasable interconnecting fastening means comprise a pair of anchor straps each secured at one end to said inner layer by stitching extending through said straps, said unitary pad and said fabric sheath, whereby the opposite ends of said anchor straps may pass through said outer layer for releasable interconnection.

8. A protective garment according to claim 6 wherein said inner layer comprises additional wing pads having separate cushioning material enclosed within a sheath, each of said wing pads having a peripheral flange projecting beyond the perimeter of its cushioning material, said flanges being secured to the peripheral flange of the sheath of said unitary pad to afford hinge-like articulation of said wing pad relative to said unitary pad.

9. A protective garment according to claim 8 wherein said wing pads are of a material having a cushion effect stiffer than the cushion effect of the unitary pad underlying said shell.

10. A protective garment according to claim 8 wherein said wing pads comprise shoulder pads and comprise a protective shell in the form of an arcuate plate of stiff, shock-resistance lightweight material having a central offset providing a reinforcement against deflection, the cushioning material of said shoulder pads corresponding in stiffness to the cushioning material of said unitary pad.

11. A protective garment according to claim 1 wherein said flexible straps are permanently connected to said plates and are of a width and stiffness so as to restrict flexing of the straps except along the hinge axis extending between said adjacent plates.

12. A protective garment according to claim 1 wherein the interconnected plate elements have a perimeter and including supplemental plate elements mounted on said inner layer beyond the perimeter of said interconnected plate elements, each of said supplemental plates being of a stiff, lightweight, shock-resistant material and having at least one pair of eyelets comprising spaced parallel slots penetrating through the associated plate elements, and anchor straps mounted on the inner layer, extending through said spaced-parallel slots and having releasable fasteners interconnecting the straps to releasably mount said supplemental plate elements on said inner layer.

13. A protective garment according to claim 1 wherein said outer shell layer comprises intermediate plate elements with overlapping edges.

14. A protective garment for the torso of a body for use by baseball umpires comprising in combination an inner layer in the forms of a flexible pad adapted to conform to the contour of the entire frontal area of the upper torso and having an inner surface adapted to confront the torso, an outer surface facing outwardly from the torso, and a perimeter defining the outlines of said inner and outer surfaces, said layer including an intermediate thickness of cushioning material between said inner and outer surfaces, an outer shell layer covering the entire frontal area of the upper torso and adapted to overlie said inner layer and comprising a plurality of interconnected plate elements, each plate element being positioned and arranged to overlie a selected area of the torso, and means interconnecting said plate elements to form a torso-fitting shell overlying said inner layer, said cushioning material adapted to distribute impacts against a given area of the outer layer over an area of the inner layer which is at least as great as said given area, said interconnecting means comprising at least one flexible strap spanning between adjacent first and second plate elements of said plurality, said strap having one end connected to one element and the other end connected to the adjacent element and being of a length to provide a clearance space between the adjacent elements to afford hinge-like displacement of said adjacent plate elements, said clearance space being less than the diameter of a baseball, said interconnecting means also including a second inflexible plate connector between two other plate elements of said plurality, said other plate elements having marginal edges positioned in confronting adjacent relation, said second connector comprising a cover element overlying the confronting marginal edges of said two other plate elements, said cover element being interconnected with each of said two other elements along said confronting marginal edges, and said plate elements and said cover element being a stiff, shock-resistant, lightweight material, said cover element of said shell providing a substantially rigid interconnection between said two other plate elements with an area of multiple thickness along each of the confronting marginal edges of said two other elements.

15. A protective garment according to claim 14 wherein said outer shell includes additional plate elements extending beyond the inner layer, said additional plate elements having individual pads secured thereto, said individual pads having inner and outer surfaces confronting respectively the torso and the additional plate element and an intermediate thickness of soft cushioning material therebetween.

16. A protective garment according to claim 15 including flexible straps connecting said additional plates to said shell, said flexible straps affording hinged movement of said additional plates relative to said shell and also affording pivotal movement of said additional plates about an axis perpendicular to one of said plates.

17. A protective garment according to claim 14 wherein said plate elements include at least one pair of eyelets comprising spaced-parallel slots penetrating through the associated plate element, said shell being connected to said inner layer by anchor straps mounted on the inner layer, extending through said spaced-parallel slots and having releasable fasteners interconnecting the straps to releasably mount said shell on said inner layer.

18. A protective garment according to claim 17 wherein said releasable interconnecting fasteners comprise complementary hook-and-loop fastener strips on said anchor straps.

19. A protect garment according to claim 14 wherein said two other plate elements comprise substantially flat marginal portions with an elevated central portion, said elevated central portion having a height greater than the thickness of said cover element.

20. A protective garment according to claim 19 wherein said raised center portions have a pair of eyelets therein in the form of spaced-parallel slots, said inner layer including anchor straps adapted to pass through said eyelets and being releasably interconnected on the outer face of said center portion to anchor said two other plate elements to said inner layer.

21. A protective garment according to claim 14, said plurality of plate elements comprising arcuately-formed elements adapted to overlie the upper part of the collarbone, said two additional plates and cover element adapted to overlie the breastbone so that the breastbone is protected by said multiple thickness of plate, and additional selected plates of said plurality adapted to overlie the rib cage.

22. A protective garment according to claim 1 wherein said adjacent plate elements comprise a first breastplate and a second plate disposed below said first plate, at least one of said plates comprising a unitary structure extending across the full width of the frontal area of the torso, the first plate having a lower edge, and the second plate having an upper edge confronting said lower edge and spaced therefrom to create said clearance space, said flexible strap extending across said edges and said clearance space, and being permanently connected to each plate adjacent its respective confronting edge.

23. A protective garment according to claim 22 wherein said confronting edges are straight and parallel to each other where said strap extends across them to preserve said limited clearance space during said hinge-like displacement.

24. A protective garment according to claim 23 wherein the confronting edge of said unitary structure is straight and horizontal across its width, and said at least one flexible strap comprises a pair of flexible straps spaced apart along the width of said horizontal confronting edge.

* * * * *